United States Patent
Costello et al.

(10) Patent No.: US 10,413,410 B2
(45) Date of Patent: Sep. 17, 2019

(54) PROFILE ALTERING TIP FOR A DELIVERY SYSTEM

(71) Applicant: Medtronic Vascular Galway, Ballybrit, Galway (IE)

(72) Inventors: Declan Costello, Ballybrit (IE); Deirdre McGowan Smyth, Ballybrit (IE)

(73) Assignee: Medtronic Vascular, Inc., Santa Rosa, CA (US)

(*) Notice: Subject to any disclaimer, the term of this patent is extended or adjusted under 35 U.S.C. 154(b) by 516 days.

(21) Appl. No.: 14/521,936

(22) Filed: Oct. 23, 2014

(65) Prior Publication Data

US 2015/0289971 A1    Oct. 15, 2015

Related U.S. Application Data

(63) Continuation-in-part of application No. 14/250,664, filed on Apr. 11, 2014, now Pat. No. 9,381,083.

(51) Int. Cl.
*A61F 2/24*    (2006.01)

(52) U.S. Cl.
CPC ................. *A61F 2/2436* (2013.01)

(58) Field of Classification Search
CPC ........... A61M 2025/09175; A61M 2025/0079; A61M 2025/0081; A61M 25/0067; A61M 25/0074; A61M 25/008; A61M 25/02; A61M 25/04; A61M 2025/0233; A61M 2025/0286; A61M 2025/0293; A61M 3/0291; A61M 2039/0261; A61F 2/2427; A61F 2/243; A61F 2/2433; A61F 2/2436; A61F 2/95; A61F 2/954; A61F 2/958; A61F 2/962; A61F 2/966; A61B 2017/3484; A61B 2017/3488; A61B 2017/3492

See application file for complete search history.

(56) References Cited

U.S. PATENT DOCUMENTS

| 7,001,406 B2* | 2/2006 | Eskuri ............. A61F 2/013 606/200 |
| 8,454,584 B2* | 6/2013 | Ducharme ......... A61B 17/0218 600/562 |
| 8,454,652 B1* | 6/2013 | Cohen ............. A61B 17/0469 606/215 |
| 2008/0065011 A1 | 3/2008 | Marchand et al. |
| 2008/0188928 A1 | 8/2008 | Salahieh et al. |

* cited by examiner

*Primary Examiner* — Eric J Rosen
*Assistant Examiner* — Mikail A Mannan
(74) *Attorney, Agent, or Firm* — Dicke, Billig & Czaja, PLLC (57) ABSTRACT

A profile altering tip is provided for a delivery system. The tip defines a first profile with a generally conical shape and a second profile with an expanded profile. During use of the delivery system, a tip profile control assembly can alter the tip from the first profile to the second profile.

14 Claims, 5 Drawing Sheets

PROFILE ALTERING TIP FOR A DELIVERY SYSTEM

CROSS REFERENCE TO RELATED APPLICATIONS

This application is a continuation-in-part application of U.S. patent application Ser. No. 14/250,664, filed Apr. 11, 2014, entitled "Profile Altering Tip for a Delivery System", the contents of which are hereby incorporated by reference in their entirety.

BACKGROUND

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With these percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). In order to access an implantation site for the valve, a tip is positioned at a distal end of the delivery system to facilitate delivery to the implantation site.

SUMMARY

One aspect of concepts presented herein relates to a device component for a delivery system. The component includes an elongate member extending from a proximal end to a distal end. A tip is coupled with the distal end of the elongate member and transitions, in response to an axially applied force applied to the elongate member, from a first, conical profile to a second, expanded profile.

Another aspect relates to a delivery system for a stent frame. The delivery system includes a retention member having a coupling structure configured to couple the stent frame to the retention member and a tip positioned distal the coupling structure. A capsule is configured to maintain the stent frame in a compressed arrangement. A tip profile control assembly includes an elongate member coupled with the tip. The elongate member extends from a proximal end to a distal end. The tip includes a tip end and a base end opposite the tip end, the elongate member transitioning the tip end from a first profile to a second profile based on a relative position of the elongate member with respect to the base end.

Yet a further aspect relates to a method of deploying a prosthetic heart valve to an implantation site. The method includes receiving a delivery system having a proximal handle and a distal tip, the system loaded with a radially expandable prosthetic heart valve having a stent frame to which a valve structure is attached. The delivery system includes a delivery sheath capsule containing the prosthetic heart valve in a compressed arrangement over an inner shaft assembly. The method further includes delivering the prosthetic heart valve in the compressed arrangement through a native valve of the patient and to the implantation site via the delivery system while the tip defines a first, tapered profile. The tip is transitioned from the first profile to a second, expanded profile. A position of the delivery sheath capsule is adjusted such that the prosthetic heart valve can expand to an expanded arrangement.

DETAILED DESCRIPTION

As referred to herein, a prosthetic heart valve as used in accordance with the various systems, devices, and methods of the present disclosure may include a wide variety of different configurations, such as a bioprosthetic heart valve having tissue leaflets or a synthetic heart valve having a polymeric, metallic, or tissue-engineered leaflets, and can be specifically configured for replacing any heart valve. Thus, the prosthetic heart valve useful with the systems, devices, and methods of the present disclosure can be generally used for replacement of a native aortic, mitral, pulmonic, or tricuspid valves, for use as a venous valve, or to replace a failed bioprosthesis, such as in the area of an aortic valve or mitral valve, for example.

In general terms, the prosthetic heart valves of the present disclosure include a frame maintaining a valve structure (tissue or synthetic), with the frame having a normal, expanded arrangement and collapsible to a compressed arrangement for loading within the delivery system. The frame is normally constructed to self-deploy or self-expand when released from the delivery system. A variety of materials can be used to form the frame, including metals (e.g., stainless steel, gold, titanium, titanium alloys) and polymers (e.g., silicone, polyethylene, polyurethane). Although embodiments discussed below reference prosthetic heart valves, concepts presented herein can be utilized with stent frames that do not have an attached valve structure (e.g., coronary stents, biliary stents).

Figure 1A:
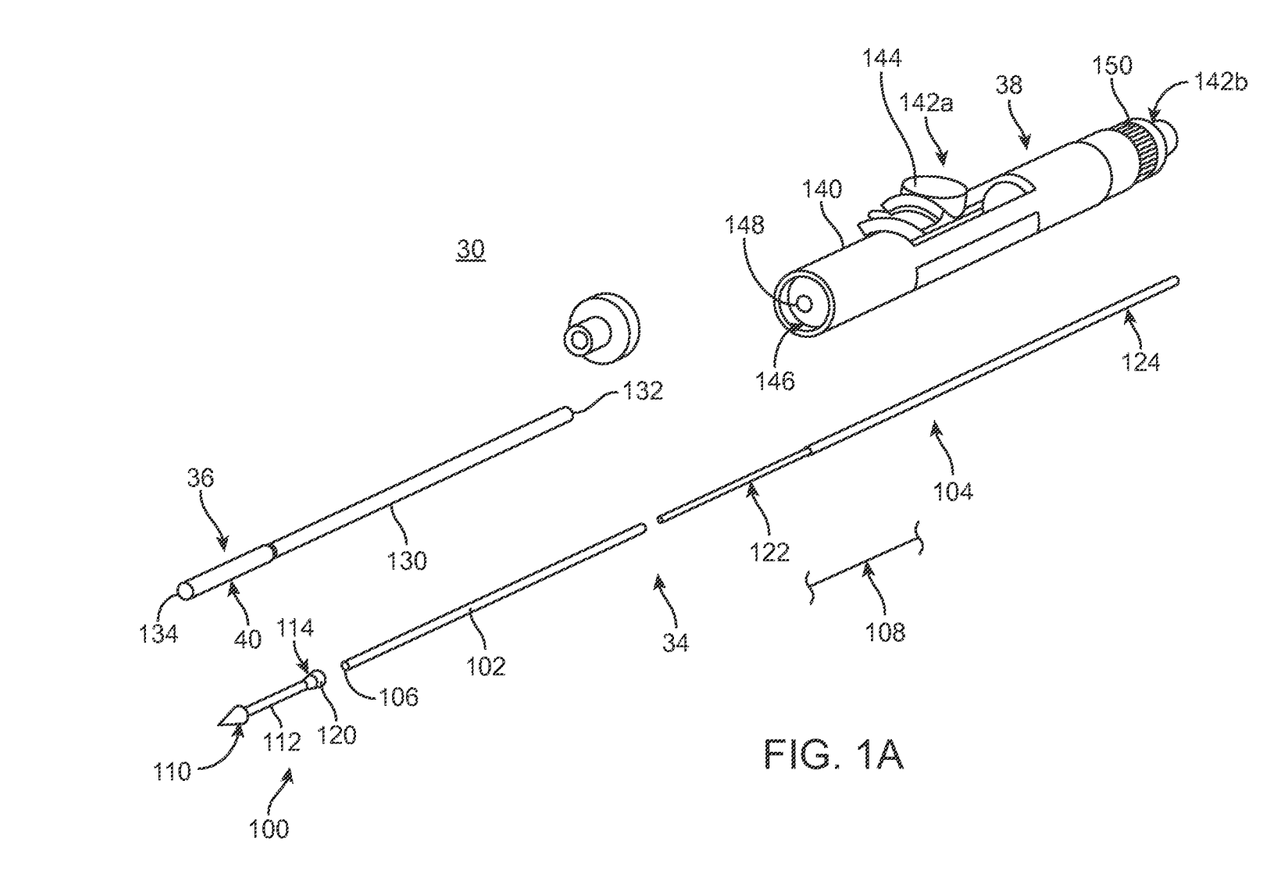
FIG. 1A is an exploded, perspective view of a delivery system.

With the above in mind, one embodiment of a transcatheter stented prosthetic heart valve delivery system 30 is shown in FIG. 1A. Although herein disclosed as applicable to a prosthetic heart valve, system 30, as well as other embodiments disclosed herein, can be used with other delivery systems, such as those utilized for stent delivery without an attached valve structure. The system 30 generally includes an inner shaft assembly 34, a delivery sheath assembly 36, and a handle 38. Details on the various components are provided below. In general terms, however, the delivery system 30 provides a loaded state in which a stent frame (not shown) is coupled to the inner shaft assembly 34 and compressively retained within a capsule 40 of the delivery sheath assembly 36. The delivery sheath assembly 36 can be manipulated to withdraw the capsule 40 proximally from the prosthetic heart valve via operation of the handle 38, permitting the frame to self-expand and release from the inner shaft assembly 34.

As a point of reference, various features of the components 34-38 reflected in FIG. 1 and described below can be modified or replaced with differing structures and/or mechanisms. Thus, the present disclosure is in no way limited to the inner shaft assembly 34, the delivery sheath assembly 36, the handle 38, etc., as shown and described below. More generally, delivery systems in accordance with the present disclosure provide features capable of compressively retaining a self-deploying, stent frame (e.g., the capsule 40) and a mechanism capable of effectuating release or deployment of the frame (e.g., retracting the capsule 40).

The components 34-38 of the delivery system 30 can assume a variety of forms appropriate for percutaneously delivering and deploying a stent frame such as a self-expanding prosthetic heart valve. For example, the inner shaft assembly 34 can have various constructions appropriate for supporting a stented prosthetic heart valve within the capsule 40. In some embodiments, the inner shaft assembly 34 can include a retention member 100, an intermediate tube 102, and a proximal tube 104. In general terms, the retention member 100 can be akin to a plunger, and incorporates features for retaining the stented prosthetic heart valve within the capsule 40 as described below. The tube 102 connects the retention member 100 to the proximal tube 104, with the proximal tube 104, in turn, coupling the inner shaft assembly 34 with the handle 38. The components 100-104 can combine to define a continuous lumen 106 (referenced generally) sized to slidably receive an auxiliary component such as a guide wire (not shown) and a tip profile control assembly 108 coupled with the retention member 100.

The retention member 100 can include a tip 110, a support tube 112, and a hub 114. The assembly 108 can be of various constructions as will be discussed in more detail below. In general, the assembly 108 can include an elongate member, a fixed member and an adjustment member that are used to alter a profile (i.e., shape) of the tip 110. The tip 110 forms or defines multiple profiles as controlled by the tip profile control assembly 108. For example, in a first profile, the tip 110 defines a nose cone having a distally tapering outer surface adapted to facilitate delivery of the capsule 40 through a patient's body to an implantation site. In particular, the tip 110 in the first profile can facilitate dilation of the implantation site (e.g., through vessels) and delivery through a native valve to be replaced (known as "valve crossing").

In a second profile, the tip 110 defines an expanded arrangement. In one example, the tip 110 forms a bulbous or round shape that is atraumatic to an internal anatomy of the patient and increases a diameter of the tip 110 approximately 10-50% of an original diameter for the tip 110. In another example, the expanded arrangement can be formed of arms that deploy outwardly and increases a diameter of the tip 110 approximately 2-3 times an original diameter for the tip 110. The second profile can be utilized during for example retraction of the capsule 40 to expose the valve and refraction of the delivery system 30. The tip 110 can further be fixed or slidable relative to the support tube 112. Alternatively, or in addition to, the tip 110 in the second profile can be used to provide tactile feedback so as to position the stent frame with respect to the native valve of the patient.

The support tube 112 extends proximally from the tip 110 and is configured to internally support a compressed, stented prosthetic heart valve generally disposed thereover, and has a length and outer diameter corresponding with dimensional attributes of the selected prosthetic heart valve. The hub 114 is attached to the support tube 112 opposite the tip 110 (e.g., an adhesive bond), and provides a coupling structure 120 (referenced generally) configured to selectively capture a corresponding feature of the prosthetic heart valve. The coupling structure 120 can assume various forms, and is generally located along an intermediate portion of the inner shaft assembly 34. In some constructions, the coupling structure 120 includes one or more fingers sized to be received within corresponding apertures formed by the prosthetic heart valve stent frame (e.g., the prosthetic heart valve stent frame can form wire loops at a proximal end thereof that are received over respective ones of the fingers when compressed within the capsule 40).

The intermediate tube 102 is formed of a flexible polymer material (e.g., PEEK), and is sized to be slidably received within the delivery sheath assembly 36. The proximal tube 104 can include, in some embodiments, a leading portion 122 and a trailing portion 124. The leading portion 122 serves as a transition between the intermediate and proximal tubes 102, 104 and thus in some embodiments is a flexible polymer tubing (e.g., PEEK) having a diameter slightly less than that of the intermediate tube 102. The trailing portion 124 has a more rigid construction, configured for robust assembly with the handle 38 such as a metal hypotube. Other constructions are also envisioned. For example, in other embodiments, the intermediate and proximal tubes 102, 104 are integrally formed as a single, homogenous tube or solid shaft.

The delivery sheath assembly 36 includes the capsule 40 and a delivery sheath shaft 130, and defines proximal and distal ends 132, 134. The capsule 40 extends distally from the delivery shaft 130, and in some embodiments has a more stiffened construction (as compared to a stiffness of the delivery shaft 130) that exhibits sufficient radial or circumferential rigidity to overtly resist the expected expansive forces of the stented prosthetic heart valve in the compressed arrangement. For example, the delivery shaft 130 can be a polymer tube embedded with a metal braiding, whereas the capsule 40 is a laser-cut metal tube. Alternatively, the capsule 40 and the delivery shaft 130 can have a more uniform construction (e.g., a continuous polymer tube). Regardless, the capsule 40 is constructed to compressively retain the stented prosthetic heart valve at a predetermined diameter when loaded within the capsule 40, and the delivery shaft 130 serves to connect the capsule 40 with the handle 38. The delivery shaft 130 (as well as the capsule 40) is constructed to be sufficiently flexible for passage through a patient's vasculature, yet exhibit sufficient longitudinal rigidity to effectuate desired axial movement of the capsule 40. In other words, proximal retraction of the delivery shaft 130 is directly transferred to the capsule 40 and causes a corresponding proximal retraction of the capsule 40. In other embodiments, the delivery shaft 130 is further configured to transmit a rotational force or movement onto the capsule 40.

The handle 38 generally includes a housing 140 and one or more actuator mechanisms 142 (referenced generally). The housing 140 maintains the actuator mechanism(s) 142, with the handle 38 configured to facilitate sliding movement of the delivery sheath assembly 36 relative to the inner shaft assembly 34, as well as alter the profile of tip 110 as controlled by the tip profile control assembly 108. The housing 140 can have any shape or size appropriate for convenient handling by a user. In one simplified construction, a first, deployment actuator mechanism 142a includes a user interface or actuator 144 slidably retained by the housing 140 and coupled to a delivery sheath connector body 146. The proximal end 132 of the delivery sheath assembly 36 is connected to the delivery sheath connector body 146. The inner shaft assembly 34, and in particular the proximal tube 104, is slidably received within a passage 148 (referenced generally) of the delivery sheath connector body 146, and is rigidly coupled to the housing 140. A second, profile actuator mechanism 142b (referenced generally) similarly includes a user interface or actuator 150 moveably maintained by the housing 140 and coupled to the tip profile control assembly 108. With this but one acceptable construction, the deployment actuator 144 can be operated to effectuate axial movement of the delivery sheath assembly 36 relative to the inner shaft assembly 34. Similarly, the profile actuator 150 can be manipulated to alter the profile of tip 110 during an implantation procedure.

Figure 1B:
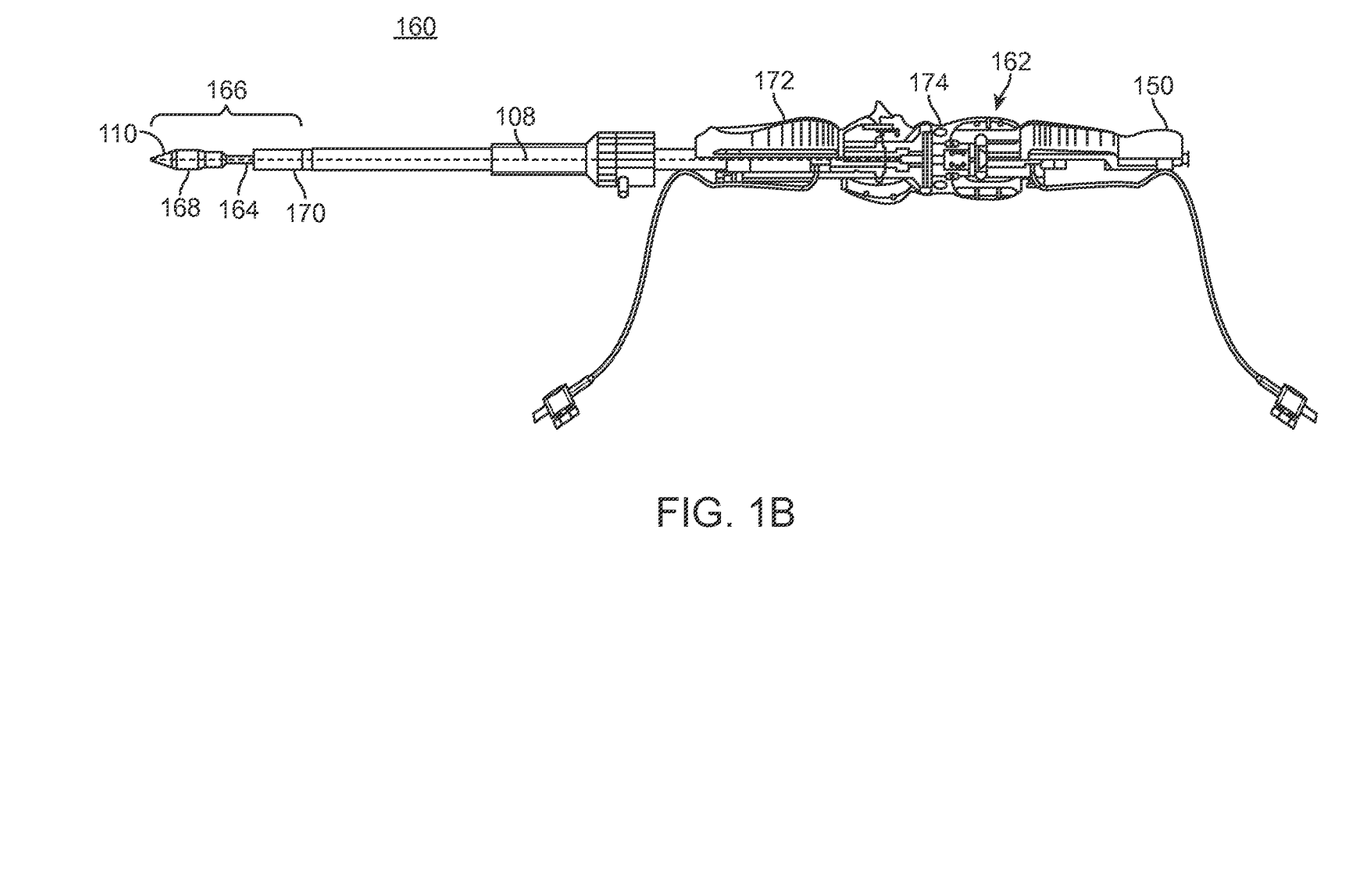
FIG. 1B is a side view of an alternative delivery system.

FIG. 1B is an alternative delivery system 160, which can include several components similar to delivery system 30 as discussed above with respect to FIG. 1A. The system 160 includes a handle 162 at a proximal end and a retention member 164 and delivery sheath capsule 166 at a distal end. The retention member 164 includes distal tip 110 and coupling structure 120 (not show in FIG. 1B) as discussed above. The delivery sheath capsule 166 includes a distal capsule portion 168 and a proximal capsule portion 170 positioned over the retention member 164 to compressively retain a stent frame of a prosthetic heart valve. A first actuator 172 on handle 162 can be operated to position distal capsule portion 168 with respect to proximal capsule portion 170, thus, allowing expansion of a portion (e.g., a distal portion) of the prosthetic heart valve. In a similar manner, an actuator 174 can be operated to position proximal capsule portion 170 with respect to distal capsule portion 168, thus allowing expansion of another portion (e.g., a proximal portion) of the prosthetic heart valve. In one embodiment, during implantation, the proximal capsule portion 170 is positioned to release a portion of the prosthetic heart valve on a first side of a native valve while the distal capsule portion 168 is positioned to release a portion of the prosthetic heart valve on an opposite side of the native valve. Similar to delivery system 30, handle 162 further maintains tip profile control actuator 150 for altering the profile of tip 110, as discussed in more detail below.

Figure 2:
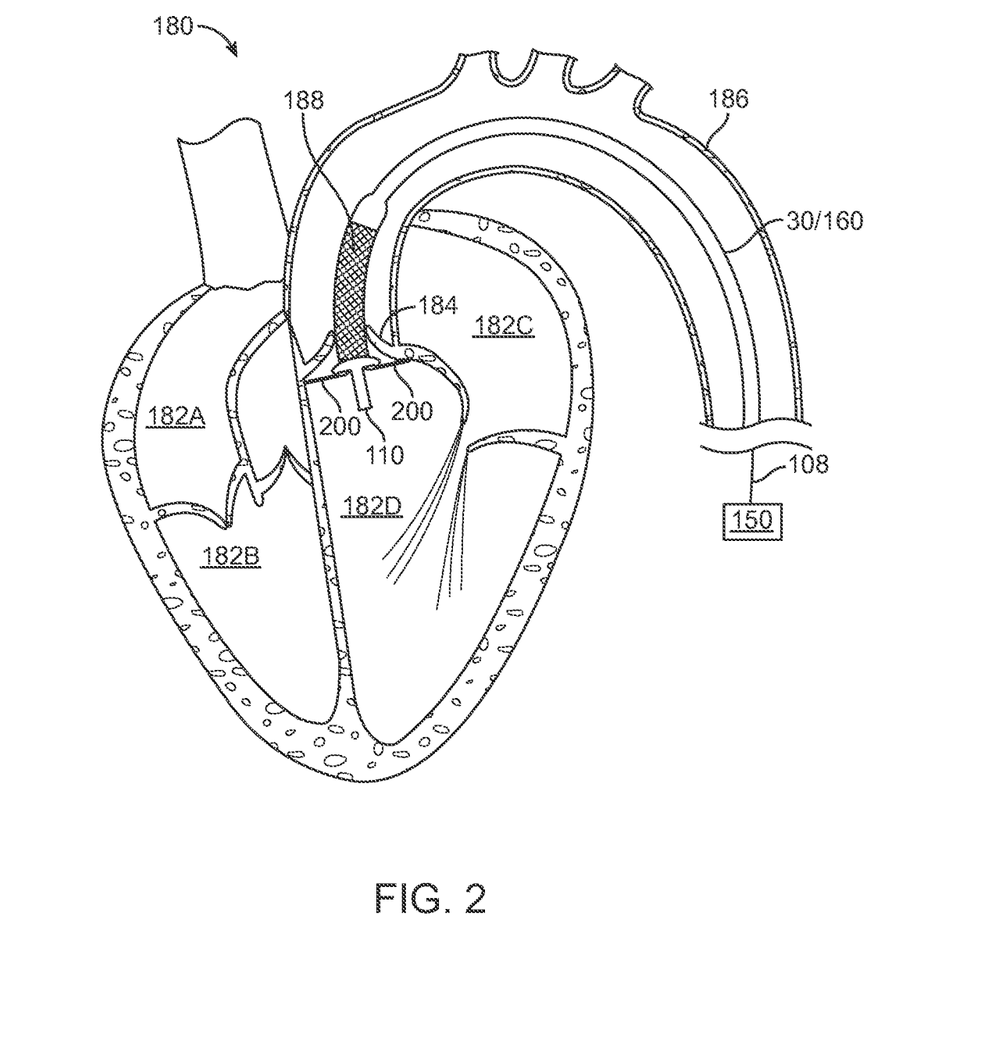
FIG. 2 is a schematic cross sectional view of a heart showing a delivery system providing a device to replace a heart valve.

Alteration of the profile of the tip 110 can be used in various ways during deployment of a stent valve to a heart. FIG. 2 is a schematic sectional view of a heart 180 that includes four chambers, namely the right atrium 182A, the right ventricle 182B, the left atrium 182C and the left ventricle 182D. Concepts presented herein can relate to replacement of any heart valves of heart 180. The example described herein relates to replacement of a native valve 184 (known as the aortic valve), positioned between an aorta 186 and left ventricle 182D of a patient. As illustrated in FIG. 2, delivery system 30/160 includes a corresponding prosthetic valve 188 has been delivered to native valve 184 through the aorta 186. In particular, tip 110 has passed through the native valve 184 and entered the left ventricle 182D.

Once the tip 110 has entered the left ventricle 182D, a profile for the tip 110 can be altered using the tip profile control assembly 108 and actuator 150 as discussed in more detail below. In one example, as illustrated in FIG. 2 and discussed in more detail with respect to FIGS. 3A-3C below, the tip 110 transitions to an expanded profile such that portions of the tip 110 can make contact with the native valve 184. In another example, as discussed with respect to FIGS. 4A-5B below, the tip 110 can transition to an expanded profile that is a round or bulbous shape that can prevent injury to the heart 180 (e.g., the left ventricle 182D) in instances where tip 110 inadvertently contacts tissue of the heart 180.

With reference to the example illustrated in FIG. 2, an operator of delivery device 30/160 can utilize contact between tip 110 and native valve 184 as an indicator of position of prosthetic valve 188 relative to the native valve 184. In instances where tip 110 makes contact with the native valve 184, an operator of the delivery system 30/160 can use the tip profile control assembly 108 and actuator 150 to expand the tip 110 to expose arms 200 on either side of the tip 110. After expansion of the arms 200, the operator can retract the delivery system 30/160 such that the arms 200 make contact with the native valve 184 (e.g., at an annulus of the valve), as illustrated in FIG. 2.

Contact between the arms 200 and the native valve 184 provides tactile feedback to the operator, indicating a relative position between the prosthetic valve 188 and the native valve 184. Placement of the prosthetic valve 188 relative to the tip 110 can be selected to provide accurate deployment of the prosthetic valve 188 with respect to the native valve 184. For example, a distance between native valve 184 and left ventricle 182D is approximately 0-4.0 millimeters. With this understanding, the delivery system 30/160 can be designed such that deployment of the prosthetic valve 188 occurs at a known position when an operator is provided with tactile feedback indicating contact between arms 200 and native valve 184. In another embodiment, axial adjustment of the arms 200 can be made so as to accommodate anatomical differences of different patients. For example, a fluoroscope can be used to visualize native valve 184 and prosthetic valve 188 during deployment, whereas an adjustment mechanism can be provided to axially adjust prosthetic valve 188 with respect to native valve 184.

Figures 3A, 3B, 3C:
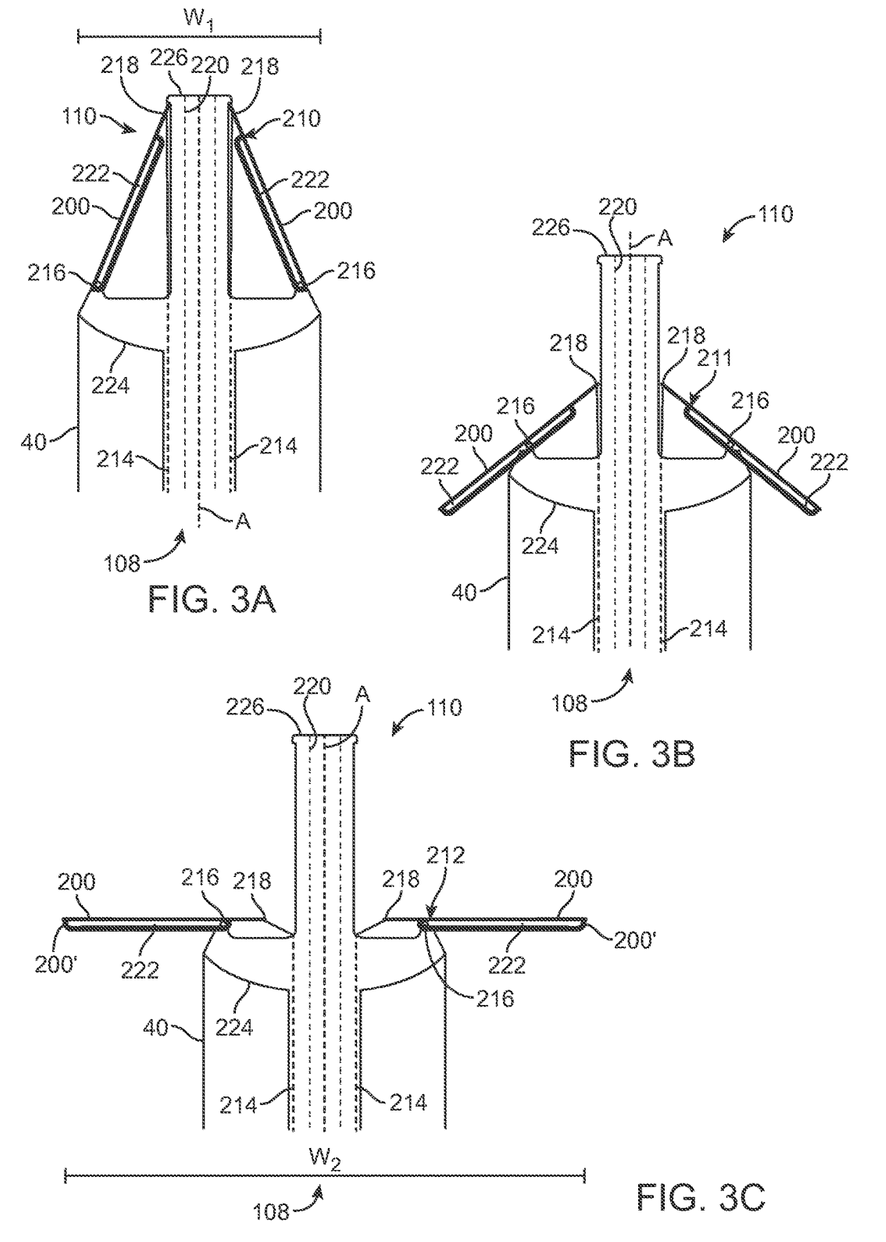
FIG. 3A is a schematic side view of an alternative tip of a delivery system in a first profile.
FIG. 3B is a schematic side view of the tip illustrated in FIG. 5A in a partially expanded profile.
FIG. 3C is a schematic side view of the tip illustrated in FIG. 5B in a second, expanded profile.

FIGS. 3A-3C schematically illustrate a tip 110 coupled with assembly 108 to transition the tip 110 from a first profile 210 (FIG. 3A), through an intermediate profile 211 (FIG. 3B) to a second, expanded profile 212 (FIG. 3C). In particular, arms 200 transition from a contracted profile to an expanded profile. Although herein illustrated as including two arms 200, any number of arms can be utilized such as three, four or more arms in order to provide sufficient width in an expanded profile to contact the native valve 184 so as to provide tactile feedback to the operator. The assembly 108 in FIGS. 3A-3C, for each arm 200, includes an elongate member 214, a fixed member 216 and an adjustment member 218. The elongate member 214 in one embodiment comprises a shaft or wire coupled to profile actuator 150 at a proximal end and extends from the housing 140 to a distal end coupled with the adjustment member 218, which herein is illustrated as a connection between the respective arm 200 and the elongate member 214. In another embodiment, the elongate member 214 can be a tube surrounding a guide wire lumen 220 and utilized to facilitate deployment of both (or more) of arms 200. Regardless of its particular form, the elongate member 214 and adjustment member 218 are movable with respect to the fixed member 216. It will be appreciated that elongate member 214 can be accommodated by a lumen within a delivery system or by other means as appreciated by those skilled in the art.

Figure 5A:
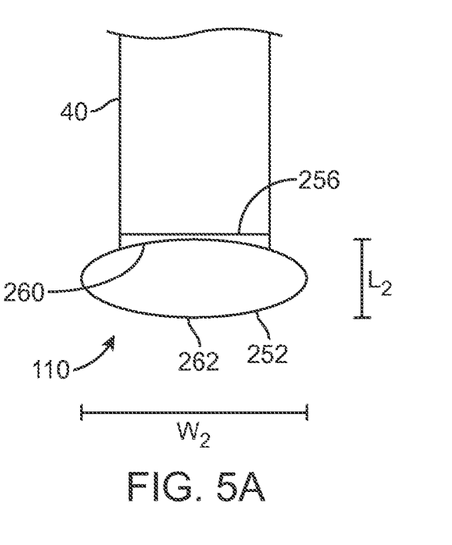
FIG. 5A is a schematic side view of the tip illustrated in FIG. 3A in a second profile, different from the first profile.
Figure 5B:
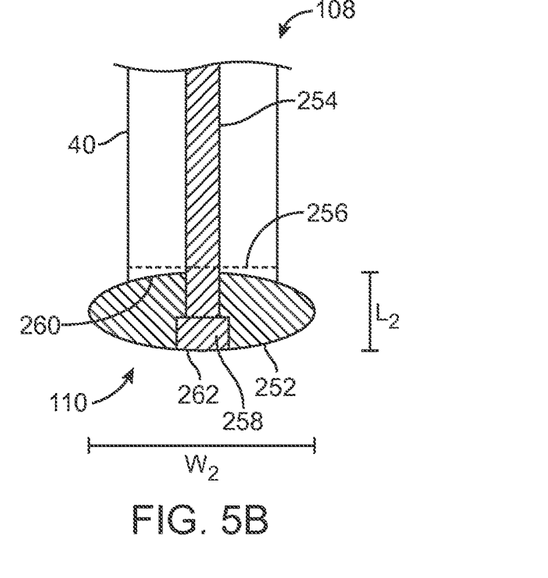
FIG. 5B is a schematic sectional view of the tip illustrated in FIG. 4A in the second profile.

By providing an axial, pulling force on the elongate member 214 (e.g., by operating profile actuator 150), the elongate member 214 and the adjustment member 218 move in an axial direction with respect to the fixed member 216, adjusting a profile of the tip 110. In an alternative embodiment, an axial, pushing force on the elongate member 214 can be used to alter the profile of the tip 110, for example by locating fixed member 216 distal the adjustment member 218. In the particular example illustrated in FIGS. 3A-3C, each fixed member 216 is embodied as a pin that communicates with a corresponding slot 222 on each arm 200. In response to an axial force provided to each elongate member 214, adjustment member 218 moves toward the fixed member 216. Due to communication between each slot 222 and each fixed member 216, each arm 200 expands outwardly as illustrated in FIGS. 5B and 5C.

The tip 110 extends from a proximal, base end 224 positioned adjacent the capsule 40 to a distal, tip end 226 where the tip 110 terminates. The base end 224 can include a lumen to accommodate the elongate member 204. In the first profile 210, each adjustment member 218 is located proximate the tip end 226 and each fixed member is coupled to the base end 224. An axial force provided by the elongate member 204 causes movement of the adjustment member 218 toward the base end 224.

A width $W_1$ of the tip 110 in the first profile 210 can be defined as a maximum distance of the tip 110 in a direction orthogonal to a central axis A of the tip 110, for example one that is coaxial with the guide wire lumen 220. In profile 210, the width $W_1$ is equal (or approximately equal) to a corresponding width of the capsule 40 (e.g., approximately 6.0-10.0 millimeters). In other embodiments, the width $W_1$ can be greater or less than the width of the capsule 40. A width $W_2$ of the tip 110 in the second profile 212 can be defined as a maximum distance of the tip 110 in a direction orthogonal to the central axis A, extending from a tip end 200' of one arm 200 to a tip end 200' of an opposite arm 200. In profile $W_2$, the width is greater than a corresponding width of the capsule 40, for example $W_2$ is in one embodiment at least twice as great as $W_1$. In another embodiment, $W_2$ is approximately 2-4 times greater (e.g., approximately 20.0-40.0 millimeters) than $W_1$. In other embodiments, the width $W_2$ can be 50% greater than the width of the capsule 40.

Figure 4A:
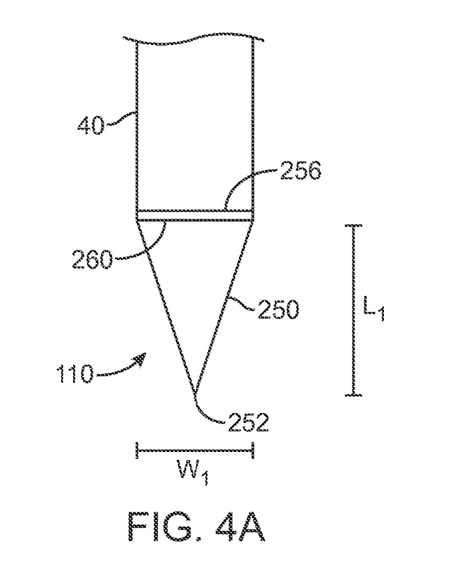
FIG. 4A is a schematic side view of a tip of a delivery system in a first profile.
Figure 4B:
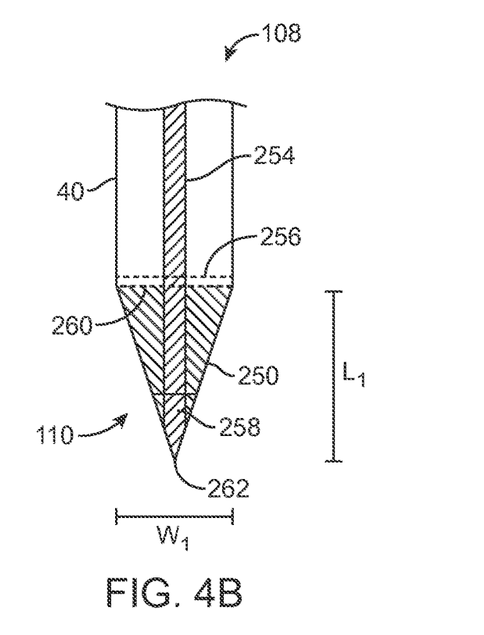
FIG. 4B is a schematic sectional view of the tip illustrated in FIG. 3A in the first profile.

FIGS. 4A and 4B illustrate close-up, schematic views of an alternative embodiment of tip 110 in a first profile 250. The tip 110 is positioned distal the capsule 40. The first profile 250 is a generally conical shape, equipped to facilitate delivery of the tip 110 through a patient's anatomy and facilitate dilation of an implantation site. FIGS. 5A and 5B illustrate close-up, schematic views of tip 110 in a second profile 252. The second profile 252 is a generally round or bulbous shape, equipped to form an atraumatic shape suitable for deploying a valve within capsule 40 and retracting the tip 110 after implantation of the valve. As discussed above with respect to FIGS. 1A and 1B, a user can operate the profile actuator 150 such that the tip profile control assembly 108 operates to alter the profile of the tip 110 between the first profile 250 and the second profile 252. In one embodiment, the tip 110 is formed of a polymeric material in a natural arrangement when in the first profile 252 and in a compressed arrangement when in the second profile 252.

The assembly 108 includes an elongate member 254, a fixed member 256 and an adjustment member 258. The elongate member 254 in one embodiment comprises a shaft or wire coupled to profile actuator 150 at a proximal end and extending from the housing 140 to a distal end coupled with the adjustment member 258. The elongate member 254 and adjustment member 258 are movable with respect to the fixed member 256. By providing an axial, pulling force on the elongate member 254 (e.g., by operating profile actuator 150), the elongate member 254 and the adjustment member 258 move in an axial direction with respect to the fixed member 256, compressing the tip 110. In an alternative embodiment, an axial, pushing force on the elongate member 254 can be used to alter the shape of the tip 110, for example by locating fixed member 256 distal the adjustment member 258. When the tip 110 is in the first profile 250 as illustrated in FIGS. 4A and 4B, the adjustment member 258 is positioned a further distance away from fixed member 256 than when the tip is in the second profile 252.

The tip 110, in one embodiment, is formed of a compressible polymer. One example polymer is sold under the tradename PEBAX®, which can be formed of a thermoplastic elastomer exhibiting a low hardness or durometer (e.g., having a hardness durometer of 75 Shore A). Other materials for tip 110 include silicone, Santoprene™, available from ExxonMobil Corporation, and/or combinations of various materials such as one or more of elastomers, rubbers, polymers. The tip 110, in one embodiment, is a polymer formed of a solid, homogenous structure capable of compression. Alternatively, the tip 110 can include a void or cut-out section so as to achieve a desired level of compressibility of the tip 110. The tip 110 extends from a proximal, base end 260 positioned adjacent the capsule 40 to a distal, tip end 262 where the tip 110 terminates. In the first profile 250, the tip 110 is in a natural arrangement that tapers from the base end 260 to the tip end 262. In contrast, in the second profile 252, the tip 110 is in a compressed arrangement that expands outwardly from the base end 260, forming a round shape that is less susceptible to causing injury to a patient's anatomy.

A length $L_1$ of the tip 110 in the first profile 250 can be defined as a distance from the base end 260 to the tip end 262. In a similar manner, a length $L_2$ of the tip 110 in the second profile 202 can also be defined as the distance from the base end 260 to the tip end. As will be appreciated, the length $L_1$ in the first profile 250 is greater than the length $L_2$ in the second profile 252. In one embodiment, a measurement of $L_2$ is approximately 50% of a measurement of $L_1$. In other embodiments, the measurement of $L_2$ can be in a range from 10% to 90% (e.g., 10%, 25%, 40%, 60%, 75%, 90%) of the measurement of $L_1$. A width $W_1$ of the tip 110 in the first profile 200 can be defined as a maximum distance of the tip 110 in a direction orthogonal to the length $L_1$. In profile 250, the width $W_1$ is equal (or approximately equal) to a corresponding width of the capsule 40. In other embodiments, the width $W_1$ can be greater or less than the width of the capsule 40. A width $W_2$ of the tip 110 in the second profile 252 can be defined as a maximum distance of the tip 110 in a direction orthogonal to the length $L_2$. In profile $W_2$, the width is greater than a corresponding width of the capsule 40, for example $W_2$ is approximately 10-50% greater than $W_1$. In other embodiments, the width $W_2$ can be equal to or less than the corresponding width of the capsule 40. In the embodiment illustrated, width $W_2$ in profile 252 is greater than width $W_1$ in profile 200. In other embodiments, $W_2$ can be equal to or less than $W_1$.

Assembling elongate member 254, fixed member 256 and adjustment member 258 to the tip 110 can be performed in a variety of different manners. In one embodiment, the tip 110 forms a central lumen to receive the elongate member 254 therein and a corresponding distal end recess to receive the adjustment member 258 therein. A proximal end of the elongate member 254 can be inserted into the central lumen and coupled with the profile actuator 150. The adjustment member 258 seats within the distal end recess such that the elongate member 254, adjustment member 258 and tip end 262 are in fixed relation relative to one another. The fixed member 256 can be formed integrally with the tip 110 or formed as a separate component, for example integral with a distal end of the capsule 40 or a separate component otherwise coupled to the base end 260 of the tip 110. Regardless of a particular construction for the fixed member 256, the elongate member 254, adjustment member 258 and tip end 262 are all movable with respect to the fixed member 256. In particular, a pulling force on a proximal end of the elongate member 254 will cause the base end 260 of the tip 110 to act against the fixed member 256. With enough pulling force, the tip end 262 (along with the adjustment member 258) moves toward the fixed member 256, causing compression of the tip 110. As such, the tip 110 is altered from the first profile 250 to the second profile 252. In an alternative embodiment, as discussed above, a pushing force can also be utilized to alter the tip 110 from the first profile 250 to the second profile 252.

Although the present disclosure has been described with reference to preferred embodiments, workers skilled in the art will recognize that changes can be made in form and detail without departing from the spirit and scope of the present disclosure.

What is claimed is:

1. A device component for a prosthetic heart valve delivery system, the component comprising:
    a tip;
    a plurality of arms moveable relative to the tip; and
    an assembly for each of the plurality of arms;
    wherein each assembly comprises an elongate member extending from a proximal end to a distal end,
    a fixed member coupled with a base end of the tip, and an adjustment member coupled with the distal end of the elongate member, wherein the respective arm is further movably connected to the fixed member, wherein the device component is configured such that in response to an axially applied force applied to the elongate members, the tip transitions from a first, conical profile to a second, expanded profile, wherein a radial spacing between a proximal end of the respective arm and the respective elongate member in the second, expanded profile is greater than the radial spacing in the first, conical profile;
    wherein for each of the assemblies a distance between the fixed member and a distal end of the respective arm varies in the expanded profile as compared to the conical profile.

2. The device component of claim 1, wherein the tip defines a lumen receiving the elongate members.

3. The device component of claim 1, wherein the first profile defines a first width defined by a maximum distance of the tip orthogonal to a length of the tip from the base end to a tip end opposite the base end, the second profile defining a second width defined by a maximum distance of the tip orthogonal to the length of the tip that is greater than the first width.

4. The device component of claim 3, wherein the second width is at least two times as great as the first width.

5. The device component of claim 1, wherein the device component is configured such that the axially applied force causes movement of each adjustment member relative to each fixed member.

6. The device component of claim 5, wherein each adjustment member is coupled with a tip end of the tip.

7. The device component of claim 1, wherein the device component is configured such that the axially applied force causes movement of each arm relative to the respective fixed member.

8. The device component of claim 7, wherein the each fixed member forms a pin that communicates with a slot of the respective arm.

9. The device component of claim 1, wherein each arm is positioned at a first angle relative to a central axis of the tip in the first profile and a second angle relative to the central axis of the tip in the second profile.

10. The device component of claim 9, wherein each arm in the second profile is orthogonal to the central axis.

11. The device component of claim 1, wherein the base end extends radially outwardly from the central axis.

12. The device component of claim 1, wherein each fixed member engages a respective one of the arms and the base end.

13. The device component of claim 1, wherein the elongate members are distal with respect to the arms in both the expanded profile and the conical profile.

14. A device component for a prosthetic heart valve delivery system, the component comprising:
    a tip;
    a plurality of arms moveable relative to the tip; and
    an assembly for each of the plurality of arms;
    wherein each assembly comprises an elongate member extending from a proximal end to a distal end,
    a fixed member coupled with a base end of the tip, and an adjustment member coupled with the distal end of the elongate member, wherein the respective arm is further movably connected to the fixed member, wherein the device component is configured such that in response to an axially applied force applied to the elongate members, the tip transitions from a first, conical profile to a second, expanded profile, wherein a radial spacing between a proximal end of the respective arm and the respective elongate member in the second, expanded profile is greater than the radial spacing in the first, conical profile; wherein for each of the assemblies, a longitudinal position of the fixed member with respect to the respective arm is variable as the tip transitions from the first, conical profile to the second, expanded profile;
    wherein the device component is configured such that, for each of the assemblies, the axially applied force causes movement of the respective arm relative to the respective fixed member;
    wherein, for each of the assemblies, the fixed member forms a pin that communicates with a slot of the respective arm; and wherein the fixed member can translate along a length of the slot.

* * * * *